United States Patent [19]
Takahashi et al.

[11] Patent Number: 4,748,198
[45] Date of Patent: May 31, 1988

[54] COATING MATERIALS FOR PROTECTING THE SURFACES OF TEETH

[75] Inventors: Masayuki Takahashi, Tokyo; Ryoji Nakazato, Tokorozawa, both of Japan

[73] Assignee: G-C Dental Industrial Corp., Tokyo, Japan

[21] Appl. No.: 39,279

[22] Filed: Apr. 17, 1987

[30] Foreign Application Priority Data

May 26, 1986 [JP] Japan .................................. 61-119156

[51] Int. Cl.$^4$ ...................... C08J 23/00; C08L 23/00; A61K 6/00
[52] U.S. Cl. ................................... 524/273; 524/271; 524/274; 523/120
[58] Field of Search ....................... 524/273, 271, 274; 523/120

[56] References Cited

U.S. PATENT DOCUMENTS

| | | | |
|---|---|---|---|
| 3,965,060 | 6/1976 | Lakshmanan | 524/271 |
| 4,189,419 | 2/1980 | Takemoto et al. | 524/273 |

FOREIGN PATENT DOCUMENTS

| | | |
|---|---|---|
| 037071 | 1/1970 | Japan . |
| 375320 | 6/1932 | United Kingdom . |
| 889709 | 3/1980 | U.S.S.R. . |

Primary Examiner—Harold D. Anderson
Assistant Examiner—Dennis R. Daley
Attorney, Agent, or Firm—Oblon, Fisher, Spivak, McClelland & Maier

[57] ABSTRACT

A coating material for protecting the surfaces of teeth is obtained by dissolving a resinous composition comprising 100 weight parts of a polystreyene resin or a high-impact polystyrene resin and 1 to 60 weight parts of rosin or a rosin derivative added thereto in an organic solvent. The resinous composition may further contain 1 to 100 weight parts of a chlorinated polymer and 1 to 100 weight parts of a coloring matter.

10 Claims, No Drawings

COATING MATERIALS FOR PROTECTING THE SURFACES OF TEETH

BACKGROUND OF THE INVENTION

1. Field of the Invention

The present invention relates to a coating material for protecting the surfaces of teeth, which has for its main object to protect the surfaces of healthy teeth against an acid etching agent used for dental treatments for preservation and restoration, and for its additional object to prevent the so-called overfilling of a restorative material, in particular, a composite resin.

2. Statement of the Prior Art

For restoration with composite resins, a carious moiety of a tooth is cut out by a dental cutting material to prepare a cavity. Thereafter, the dentin is subjected to partial demineralization with an acid etching agent for rough plasticization at a pre-treatment step for enhancing the adhesion between the dentin and the restorative composite resin, followed by application of a bonding material. However, since the acid etching agent used at such a pre-treatment step is a highly fluid aqueous solution of phosphoric or citric acid, a problem arises that even the healthy enamel surrounding the cavity is subjected to demineralization with the result that the surface of a tooth is made cloudy and rough unnecessarily.

The conventional coating material for protecting the surface of teeth is designed to form a protecting film composed mainly of a copolymer based on vinyl acetate and vinyl chloride. However, such a coating material offers a problem that since the protecting film per se obtained therefrom is soft and easily "extensible" in its nature, it cannot be cut out well by a dental cutting tool at the time of cavity preparation, thus leaving behind an uncut portion and causing refuse to be mingled in the inside of the restorative composite resin at the time of filling. This obstructs the distribution of that coating material. Further, since the coating film is of a dull color tone, it is difficult to distinguish it from the cavity edge. Hence, a coating film of a vivider color tone is still demanded by dentists.

SUMMARY OF THE INVENTION

The coating material for protecting the surfaces of teeth should have the following two indispensable properties:

1. It should neither be damaged by nor premeated by a dental etching agent, and should protect the surface of a healthy tooth.
2. It should show well adhesion to the surface of a tooth, and should not be peeled off therefrom during composite resin restoration.

In accordance with the present invention, a resinous composition meeting the aforesaid basic requirements is obtained by adding rosin or a rosin derivative to a polystyrene resin. As a result of studies made of additives to solve the problems as already mentioned, it has been found that the following additional properties are obtained.

3. When the invented coating material is applied around a cavity and cut out by a dental cutting tool, a sharp cutting edge or section is obtained without any uncut portion.
4. After filling of the composite resin, an extra portion of the protecting film can easily be removed with a toothbrush or Robinson brush.
5. The protecting film can be colored to a higher concentration for easy discrimination.
6. It is very unlikely that the colored protecting film may contaminate the restorative composite resin.

Immediately upon coated around a cavity, the coating material for protecting the surfaces of teeth according to the present invention forms rapidly a protecting film, which is effective for preserving the healthy tooth substance from an unnecessary demineralization by a dental etching agent used at the pre-treatment step for compsite resin restoration.

Further, when the coating material according to the present invention is applied on from a tooth to gingiva, the thus coated film keeps any exudation from the gingiva and thereby fulfills a simplified damp-proofing function, which makes a great deal of contribution to assured composite resin restoration. Such a film coated on the gingiva can easily be removed by brushing with a toothbrush. For easier discrimination of the protecting film, a coloring matter may be added to the resinous composition according to the present invention for coloration. The thus colored film facilitates cavity preparation, and indicates more clearly of the cavity portion during composite resin filling, so that the cavity preparation can be carried out while observing whether or not the restorative resin overflows from the cavity. In addition, since it is easy to identify through the coloring matter contained in the protecting film the overfilling portion over which the restorative material overflows and is set, thus presenting one cause of marginal breakage, it is possible to remove an extra portion of the restorative material with that portion of the film as a guide.

The coating material for protecting the surfaces of teeth having such functions satisfies the need of dentists desiring to preserve tooth substance as long as possible, and is thus of great usefulness.

DETAILED DESCRIPTION OF THE INVENTION

Coating films composed mainly of a polystyrene resin or a high-impact polystyrene resin excel in water resistance, acid resistance and solvent resistance, as proven by cutting under water pouring, immersing in a dental etching agent and a dental bonding agent or a high-boiling methacrylate ester such as a composite resin monomer, respectively. In addition to such excellent properties, to afford excellent adhesion to the surfaces of teeth and excellent cuttability by a dental cutting tool to such coating films is enabled by a combination of the following ingredients in accordance with the present invention. In other words, it has been found that the addition of rosin or a rosin derivative is very effective for improving the adhesion between the films and the surfaces of teeth, and that the addition of a chlorinated polymer is also very effective for improving the cuttability by a dental cutting tool, and gives a sharp cut area.

In accordance with the present invention, a coloring matter, preferably containing fluorescence, is further added to obtain a protecting film which is extremely discriminative.

The present invention will now be explained in detail.

According to the present invention, a resinous composition containing as the main component a polystyrene resin or a high-impact polystyrene resin containing synthetic rubber is dissolved in an organic solvent. Upon coated on the surface of a tooth, the organic solvent is volatilized off from the resulting solution to form a film.

When rosin or a rosin derivative has been added to the resinous composition, the adhesion of the resulting protecting film to the surface of a tooth is further improved. Thus, the adhesion and durability of the protecting film are sufficiently assured even during a series of restoration operations comprising cavity preparation under water pouring with a dental cutting material, drying with compressed air, application of an acid etching agent, water washing and drying.

Referring to the cuttability of the protecting film by a dental cutting material, which has been the most important problem in the prior art, it has been found that the flexibility and "extensibility" of the protecting film are limited or improved by adding a chlorinated polymer to the resinous composition according to the present invention. In other words, when a cavity is prepared by a dental cutting tool, excellent cuttability is realized, as proven in terms of a sharp cut area without any uncut portion or refuse.

In accordance with the present invention, a coloring matter may also be added to the resinous composition for easier discimination of the protecting film. As a result of intensive and extensive studies made of a series of composite resin restoration operations carried out with a variety of coloring matters added, it has been found that when a pigment coated with a styrene.rosin-modified maleic acid resin is added as the coloring matter alone or in combination with a green pigment, a protecting film is obtained which does not only show excellent dispersibility, but can also be crisply cut to provide a sharp cut area. This accounts for, it is considered, the fact that the resin-coated coloring matter is present as a filler in the protecting film, limits properly the "linking" or "extension" of the protecting film, and allows easy tearing-off of the protecting film. When the coloring matters used include a fluorescent pigment, there is obtained an additional advantage that the protecting film is more discriminative, that is, when the protecting film is exposed to light from a visible-light polymerization lamp for composite resins used in dentistry (wavelength 400–600 nm), it emits strong fluoresence, through which the presence of uncut portions or mingling of refuse into the restorative material can immediately be detected.

The present invention will now be explained in detail with reference to the details of its construction.

The coating material for protecting the surfaces of teeth according to the present invention is a film-forming composition obtained by dissolving a resinous composition in an organic solvent, said composition containing a polystyrene resin or a high-impact polystyrene resin as the main component.

Such a polystyrene or high-impact polystyrene resin should be selected, while taking into consideration the water resistance required for the film for protecting the surfaces of teeth, the acid resistance to a dental etching agent and the solvent resistance to a high-boiling methacrylate ester used as a dental bonding material or composite resin monomer. The present invention relates to a resinous composition obtained by adding 1 to 60, preferably 5 to 40 weight parts of rosin or a rosin derivative to 100 weight parts of such a polystyrene or high-impact polystyrene resin to enhance its adhesion to teeth.

Further, 1 to 100, preferably 5 to 80 weight parts of a chlorinated polymer may be added to the resinous composition to improve its cuttability by a dental cutting material, while 1 to 100, preferably 3 to 80 weight parts of a coloring matter may be added to the resinous composition for easier identification of the protecting film. The resinous composition is dissolved in an organic solvent for application to the surfaces of teeth, etc.

The organic solvents to be employed in the present invention include ethyl acetate, n-propyl acetate, isopropyl acetate, n-butyl acetate, isobutyl acetate, acetone, ethyl ether, isopropyl alcohol, ethanol, methylene chloride, ethylene chloride and chloroform, which may be used alone or in combination. For application to the surfaces of teeth, the resinous composition may be dissolved in such a solvent at a concentratin of 1 to 40 weight %.

When the resinous composition of the present invention is dissolved in an organic solvent and coated on the surface of a tooth, the rosin or its derivative added thereto has the property of showing strong adhesion to the tooth substance and adhering thereto, and forming a hard film thereon, after the organic solvent has been volatilized off. Since the rosin or its derivative tends to lower the rate of volatilization of the organic solvent, it is added and used in a proportion of 1 to 60, preferably 5 to 40 weight parts per 100 weight parts of the polystyrene or high-impact polystyrene resin. That is, when the rosin or its derivative is used in an amount of less than 1 weight part, it provides a protecting film which is so poor in the adhesion to the surface of a tooth that it may be released therefrom during cavity preparation under water pouring or water washing-air gun drying. On the other hand, use of the rosin or its derivative in an amount of higher than 60 weight parts is practically unsuitable, since the resulting film does not only show reduced or limited durability with respect to an alcohol contained in a dental bonding material, but does also require a longer drying period of time and, nonetheless, offers a sticky problem. The rosin or its derivative to be used in the present invention includes rosin, polymerized rosin, rosin-modified maleic acid resin and rosin-modified glycerin ester, rosin-modified pentaerythritol ester.

When the resinous composition dissolved in an organic solvent is coated into a protecting film, the chlorinated polymer added thereto allows that film to be very hard but brittle, and improves the resistance of that film to not only water and acids but also solvents such as high-boiling methacrylate esters, for instance, a dental bonding material and a composite resin monomer. The chlorinated polymer is added and used in a proportion of 1 to 100, preferably 5 to 80 weight parts per 100 weight parts of the polystyrene or high-impact polystyrene resin. When the chlorinated polymer is used in an amount of less than 1 weight part, the resulting protecting film is so flexible that any sharp cut area is not obtained, since it "extends" during cutting. On the other hand, use of that polymer in an amount of higher than 100 weight parts is practically unsuitable, since its compatibility with the polystyrene or high-impact polystyrene resin becomes poor so that separation of a liquid phase takes place, thus giving a protecting film in the form of oil droplets. The chlorinated polymer to be used in the present invention includes chlorinated polyethylene, chlorinated polypropylene, chlorinated rubber and so on.

The coloring matter to be added to the resinous composition for easier discimination of the protecting film should be selected, while care is taken of the fact that it should neither dissolve nor diffuse in an alcohol or a high-boiling methacrylate contained in a dental bonding material or composite resin. That is to say, suitable coloring matters are pigments, or dyes or pigments coated with resins. For further easier discrimination of the protecting film, these coloring matters may be used in combination with fluorescent coloring matters. This is very convenient, since the presence of the protecting film can immediately be ascertained with light from a visible-light polymerization lamp for composite resins. The coloring matters to be used are preferably less harmful to the human body, and may include Sudan II, rhodamine B acetate, indigo, Sudan blue B, phthalocyanine blue, phthalocyanine green, chromophthal blue, chromophthal green, carbon black and iron oxides or those which may be coated with resins such as styrene.-rosin-modified maleic acid resin. In addition, they may be used in combination with fluorescent coloring matters such as basic yellow HG, brilliant sulfofurabin FF, and synleuch color FZ 5005 and others. These coloring matters are used in a proportion of 1 to 100, preferably 3 to 80 weight parts per 100 weight parts of the polystyrene or high-impact polystyrene resin. Use of the coloring matters in an amount of less than 1 weight parts is practically not suitable, since their concentration is so low that it is difficult to identify the protecting film. Use of the coloring matters in an amount of higher than 100 weight parts is practically not suitable neither, since they are exposed on the protecting film, an increase excessively the thickness of the coated film, thus causing a lowering in application of coatings.

EXAMPLES OF THE INVENTION

Table 1 shows the results of the examples of the present invention carried out under the following conditions. It is to be understood, however, that the present invention is not limited to numerical values set forth therein.

EXAMPLES 1 TO 8 AND COMPARISON EXAMPLES 1 TO 5

After teeth extracted from patients had been coated thereon with the coating materials for protecting the surfaces of teeth having the compositions as specified in Table, a series of operations were carried out, which involved cavity preparation under water pouring, air gun drying, application of an etching agent, water washing-air gun drying, application of a bonding material, air gun drying, filling of a composite resin, cleaning and polishing, thereby to make evaluation of the following six properties required for the coating materials for protecting the surfaces of teeth.

1. Acid Resistance: evaluated in terms of whether or not the surfaces of healthy teeth are subjected to demineralization when the dental etching agent is applied thereon.
2. Adhesion: evaluated in terms of whether or not the film formed on teeth and the surface of gingiva is released therefrom.
3. Cuttability: evaluated in terms of whether or not a sharp cut area can be formed during cavity preparation with a cutting tool.
4. Contaminative Property: evaluated in terms of whether or not the coloring matter finally passes from the protecting film into the composite resin.
5. Cleaning Property: evaluated in terms of whether or not the protecting film can be removed under water pouring with a dental toothbrush.
6. Discriminative Property: evaluated in terms of whether or not the colored protecting film can be discriminated from the teeth or composite resin during manipulation.

| | (weight parts) | | | | | | | | | | | | |
|---|---|---|---|---|---|---|---|---|---|---|---|---|---|
| | Example | | | | | | | | Comparison Example | | | | |
| | 1 | 2 | 3 | 4 | 5 | 6 | 7 | 8 | 1 | 2 | 3 | 4 | 5 |
| Per 100 weight parts of ethyl acetate | | | | | | | | | | | | | |
| Polystyrene | 10 | 10 | 10 | 10 | 10 | 10 | 10 | 10 | | 10 | 10 | 10 | 10 |
| Chlorinated polyethylene | | 2 | | 2 | 2 | 2 | 10 | 0.1 | | 2 | 12 | | |
| Chlorinated rubber | | | 2 | | | | | | | | | 12 | |
| Polymerized rosin | 2 | 2 | 2 | 2 | 2 | 2 | 6 | 0.1 | | | | | 10 |
| Vinyl acetate.vinyl chloride copolymer | | | | | | | | | 8.5 | | | | |
| Vinyl acetate.vinyl chloride.maleic anhydride copolymer | | | | | | | | | 1.5 | | | | |
| γ-methacryloxypropyl trimethoxy silane | | | | | | | | | 0.5 | | | | |
| Oil blue-2N (Dye) | | | | | | | | | | 1 | | | |
| Lemon yellow (Fluorescent pigment) | | | | 4 | 4 | | 4 | | | 3 | | | 4 |
| Phthalocyanine blue | | | | 2 | | 2 | | 0.1 | 0.5 | | | 15 | |
| Phthalocyanine green treated with styrene.rosin modified maleic acid resin | | | | | 2 | 2 | | | | | 15 | | 2 |
| (1) Acid resistance | ⊙ | ⊙ | ⊙ | ⊙ | ⊙ | ⊙ | ⊙ | ⊙ | ⊙ | ⊙ | ⊙ | ⊙ | ⊙ |
| (2) Adhesion | ⊙ | ⊙ | ⊙ | ⊙ | ⊙ | ⊙ | △ | △ | ⊙ | X | X | X | △ |
| (3) Cuttability | X | ○ | ○ | ○ | ⊙ | ⊙ | △ | △ | X | △ | X | X | X |
| (4) Contaminative property | ⊙ | ⊙ | ⊙ | ○ | ○ | ○ | ⊙ | ⊙ | ○ | X | X | X | X |
| (5) Cleaning property | ⊙ | ○ | ○ | ○ | ○ | ○ | ○ | ⊙ | ○ | ○ | ○ | ○ | ○ |
| (6) Discriminative property | X | X | X | ⊙ | ⊙ | ○ | X | △ | X | ⊙ | ⊙ | ⊙ | ⊙ |

Evaluation
⊙: Excellent
○: Good
△: Fairly good
X: Bad

The present invention relates to a coating material for protecting the surfaces of teeth, which is improved in respect of its cuttability by a dental cutting material and its discriminative property, and has the following various effects in clinical applications.

1. In the case where cavity preparation is carried out with a dental cutting material of the carbide bar type, diamond-pointed fine grain type or ultra-fine grain type, for instance, if the coating material for protecting the surfaces of teeth according to the present invention is coated around a cavity, it is then possible to form a protecting film adhering to the edge of the cavity on the surface of a tooth with no fear of any uncut portion since that film possesses sharp cuttability.
2. Since a dental etching agent such as an aqueous solution of phosphoric or citric acid does not permeate through the protecting film obtained according to the present invention, the surface of a healthy tooth surrounding a cavity is protected against acid attack.
3. In filling of composite resin, the so-called overfilling portion over which an amount of composite resin overflows from a cavity and is cured can clearly be indicated by the colored film, thus assuring removal of that overfilling portion at the time of polishing.
4. Since a fluorencent coloring matter is used for the coloration of the protecting film, it is of a vivid color tone and easily discriminative. In addition by exposing for a short period of time to light from a visible light (wavelength: 400 to 600 nm) polymerization lamp used in dentistry, the protecting film gives out strong fluorescence, through which the presence of any uncut portion or mingling of cutting refuse thereinto can immediately be detected.
5. The coating material to prevent liquid permeation is coated on gingiva to form the protecting film on the surface thereof, which provides a simplified damp-proofing function for keeping any exudation from the gingiva. After assured composite resin filling has been carried out under the damp-proofing action, the protecting film is easily be removed as by brushing with a toothbrush.

What is claimed is:

1. A coating material for protecting the surfaces of teeth, wherein a resinous composition comprising 100 weight parts of a polystyrene resin or a high-impact polystyrene resin and 1 to 60 weight parts of rosin or a rosin derivative selected from the group consisting of polymerized rosin, rosin-modified maleic acid resin, rosin-modified glycerin ester and rosin-modified pentaerythritol ester, and 1 to 100 weight parts of a chlorinated polymer added thereto is dissolved in an organic solvent.

2. A coating material as claimed in claim 1, wherein said chlorinated polymer is a chlorinated polyolefin.

3. A coating material as claimed in claim 1, wherein said chlorinated polymer is a chlorinated rubber.

4. A coating material as claimed in any one of claims 1 to 3, wherein said resinous composition is dissolved at a concentration of 1 to 40 weight % in an organic solvent.

5. A coating material for protecting the surfaces of teeth, wherein a resinous composition comprising 100 weight parts of a polystyrene resin or a high-impact polystyrene resin and 1 to 60 weight parts of rosin or rosin derivative selected from the group consisting of polymerized rosin, rosin-modified maleic acid resin, rosin-modified glycerin ester and rosin-modified pentaerythritol ester, 1 to 100 weight parts of a chlorinated polymer and 1 to 100 weight parts of a coloring matter added thereto is dissolved in an organic solvent.

6. A coating material as claimed in claim 5, wherein said chlorinated polymer is a chlorinated polyolefin.

7. A coating material as claimed in claim 5, wherein said chlorinated polymer is a chlorinated rubber.

8. A coating material as claimed in any one of claims 5 to 7, wherein said coloring matter comprises a coloring matter of fluorescence or a color tone capable of clearly indicating the boundary between the surface portion to be protected and the cavity portion, and discriminating therebetween.

9. A coating material as claimed in claim 5, wherein said coloring matter comprises at least one of coloring matters coated with a styrene.rosin-modified maleic acid resin.

10. A coating material as claimed in claim 5, wherein said resinous composition is dissolved at a concentration of 1 to 40 weight % in an organic solvent.

* * * * *